(12) United States Patent
Muehlfeld et al.

(10) Patent No.: US 11,696,542 B1
(45) Date of Patent: Jul. 11, 2023

(54) SYSTEMS AND METHODS OF SEED PRODUCTION PLANT COUNTING USING AERIAL IMAGES

(71) Applicant: Sentera, Inc., Minneapolis, MN (US)

(72) Inventors: Andrew Muehlfeld, Minneapolis, MN (US); Elliott Imhoff, Minneapolis, MN (US)

(73) Assignee: Sentera, Inc., St. Paul, MN (US)

( * ) Notice: Subject to any disclaimer, the term of this patent is extended or adjusted under 35 U.S.C. 154(b) by 51 days.

(21) Appl. No.: 16/860,174

(22) Filed: Apr. 28, 2020

(51) Int. Cl.
*A01H 6/00* (2018.01)
*A01H 6/46* (2018.01)
*A01B 79/00* (2006.01)
*A01B 76/00* (2006.01)
*A01H 1/02* (2006.01)

(52) U.S. Cl.
CPC ............ *A01H 6/4684* (2018.05); *A01B 76/00* (2013.01); *A01B 79/005* (2013.01); *A01H 1/02* (2013.01)

(58) Field of Classification Search
CPC ..... A01H 6/4684; A01B 76/00; A01B 79/005; A01H 1/02
See application file for complete search history.

(56) References Cited

U.S. PATENT DOCUMENTS

| | | | |
|---|---|---|---|
| 2014/0010414 A1* | 1/2014 | Lejeune et al. | A01G 22/60 382/110 |
| 2019/0246586 A1* | 8/2019 | Cannon et al. | C12N 15/8218 |
| 2019/0258859 A1* | 8/2019 | Baynes et al. | A01B 49/06 |
| 2021/0127610 A1* | 5/2021 | Lidor-Nili et al. | A01H 1/06 |
| 2021/0272255 A1* | 9/2021 | Barrick et al. | A01B 79/005 |
| 2021/0295041 A1* | 9/2021 | Guzhva et al. | G06K 9/2018 |

* cited by examiner

*Primary Examiner* — Pakee Fang
(74) *Attorney, Agent, or Firm* — Hamre, Schumann, Mueller & Larson, P.C.

(57) ABSTRACT

Techniques are described for generating population counts for seed production plants based on one or more images obtained from a camera on an aerial vehicle including, but not limited to, UAVs. The image(s) is processed to identify the plurality of rows of seed production plants, classify each one of the identified rows as either male or female, and produce a count of the number of seed production plants in the male rows and produce a count of the number of seed production plants in the female rows. The seed production plants can be corn seed plants or any other type of seed production plant in which male and female seed production plants can be distinguished from one another based on one or more aerial images.

21 Claims, 13 Drawing Sheets

Fig. 6

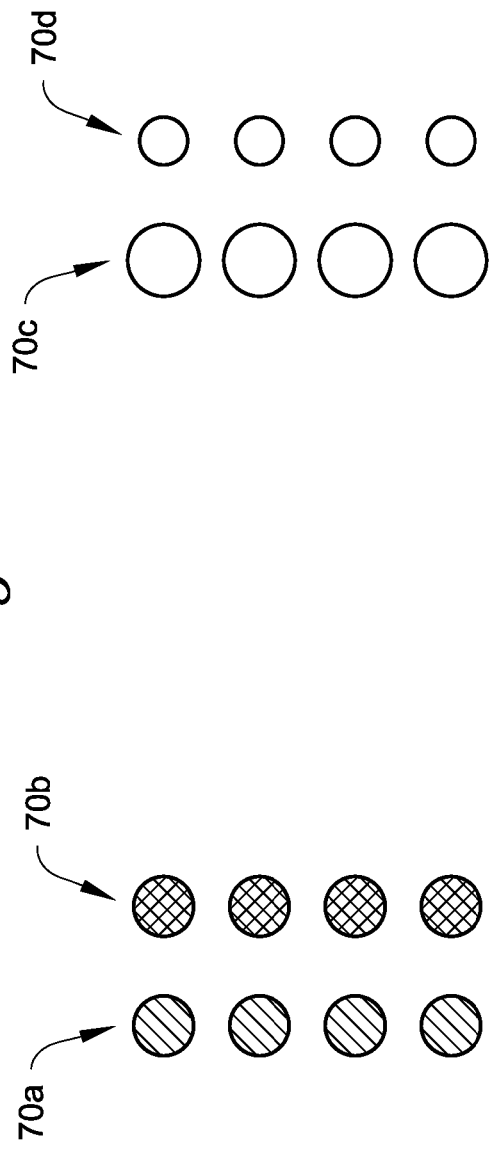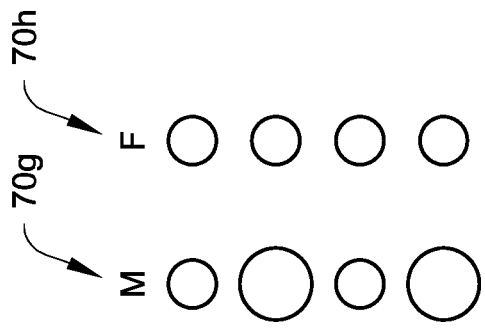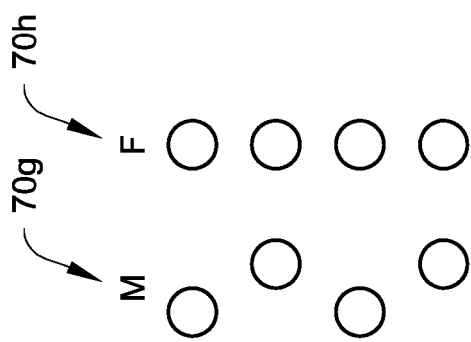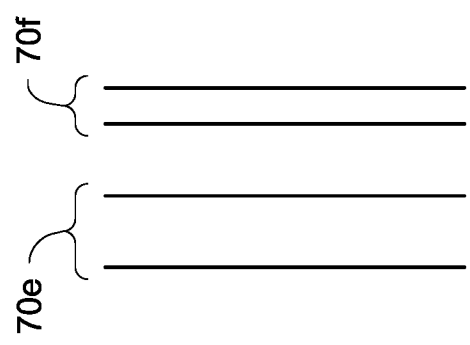
Fig. 7A
Fig. 7B
Fig. 7C
Fig. 7D-1
Fig. 7D-2

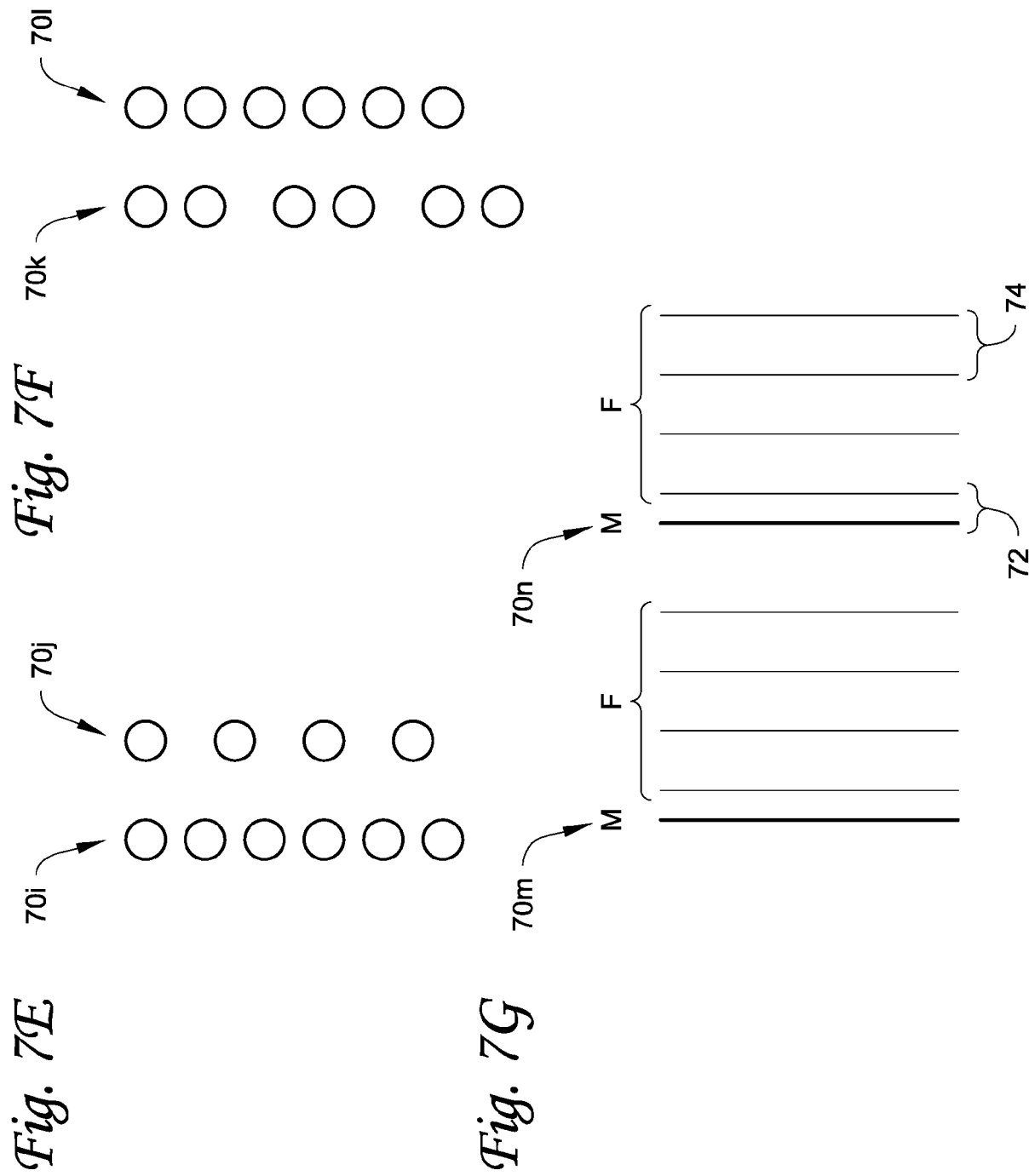

SYSTEMS AND METHODS OF SEED PRODUCTION PLANT COUNTING USING AERIAL IMAGES

FIELD

This technical disclosure relates to aerial imaging of seed production fields, for example for corn seed, and techniques for generating population counts of seed production plants based on one or more images obtained from cameras on aerial vehicles including, but not limited to, unmanned aerial vehicles (UAVs).

BACKGROUND

Farmers grow corn to sell as grain on the open market. Farmers buy their corn seed from seed producers. Seed producers grow hybrid seed corn in a special way, often with male and female seed plants. Typically, male and female seed plant are arranged in rows, with all plants in a row intended to be the same gender. Commonly there is a repeating pattern across a field of one or two male rows followed by four or five female rows. Seed producers are interested in counting the male seed plants and the female seed plants to make replanting decisions, as a factor in estimating yield, and for other reasons.

SUMMARY

Techniques are described herein for generating population counts for seed production plants based on one or more images obtained from a camera on an aerial vehicle including, but not limited to, UAVs. The seed production plants can be corn seed plants or any other type of seed production plant in which male and female seed production plants can be distinguished from one another based on one or more aerial images.

In operation, the aerial vehicle is flown over a seed production field that includes a plurality of rows of seed production plants. The aerial vehicle captures one or more images of the seed production field. Analysis is then performed based on the one or more images in order to generate the count(s). A count can be generated of the seed production plants in rows that are identified as female. This count may also be referred to as a count of the female seed production plants. In another embodiment, a count can be generated of the seed production plants in rows that are identified as male. This count may also be referred to as a count of the male seed production plants. In still another embodiment, both the count of the seed production plants in rows that are identified as female and the count of the seed production plants in rows that are identified as male can be generated.

The image that is analyzed can be a global image or a local image. A global image can be a single image of the field where the single image corresponds to the entire field of view of the camera that obtained the image. A global image can also be a mosaicked image that is derived from two or more images that are mosaicked or combined together to form the global image. A local image is a portion of a global image where the portion is separately analyzed from another portion(s) of the global image. The local image may also be referred to as a sub-image or sub-region of the global image.

In one embodiment, a method of seed production plant population counting in a seed production field that includes a plurality of rows of seed production plants is provided. The method can include receiving at least one image of the seed production field, the at least one image being obtained by an aerial vehicle. The at least one image, which can be a global image or a local image, is then processed to: identify the plurality of rows of seed production plants; classify each one of the identified rows as either male or female; and produce a count of the number of seed production plants in the male rows and/or produce a count of the number of seed production plants in the female rows. The count(s) is/are then stored on a suitable data storage mechanism, for example on a tangible computer-accessible storage medium.

In another embodiment, a method of corn seed production plant population counting in a corn seed production field that includes a plurality of rows of male and female corn seed production plants is provided. The method can include flying an unmanned aerial vehicle over the corn seed production field, and capturing at least one image of the corn seed production field using a camera on the unmanned aerial vehicle and storing the at least one image. The at least one image, which can be a global image or a local image, is then processed to produce a count of the number of male corn seed production plants and/or produce a count of the number of female corn seed production plants. The count(s) is/are then stored on a suitable data storage mechanism, for example on a tangible computer-accessible storage medium.

In another embodiment, a system of seed production plant population counting in a seed production field that includes a plurality of rows of seed production plants is provided. The system can include an aerial vehicle having at least one camera, and a tangible computer-accessible storage medium that stores an image of the seed production field obtained by the at least one camera. The system also includes a processor that uses the image, which can be a global image or a local image, to identify the plurality of rows of seed production plants, classifies each one of the identified rows as either male or female, and produces a count of the number of seed production plants in the male rows and/or produces a count of the number of seed production plants in the female rows.

DRAWINGS

FIG. 1 depicts a UAV flying over a seed production field.

FIG. 2 schematically depicts example components of a UAV described herein together with an example of a system separate from the UAV that can process image data obtained by the UAV.

FIG. 6 depicts an image of a global row analysis algorithm.

FIGS. 7A-G illustrate different example of classifying rows as male and female rows.

Figure 8:
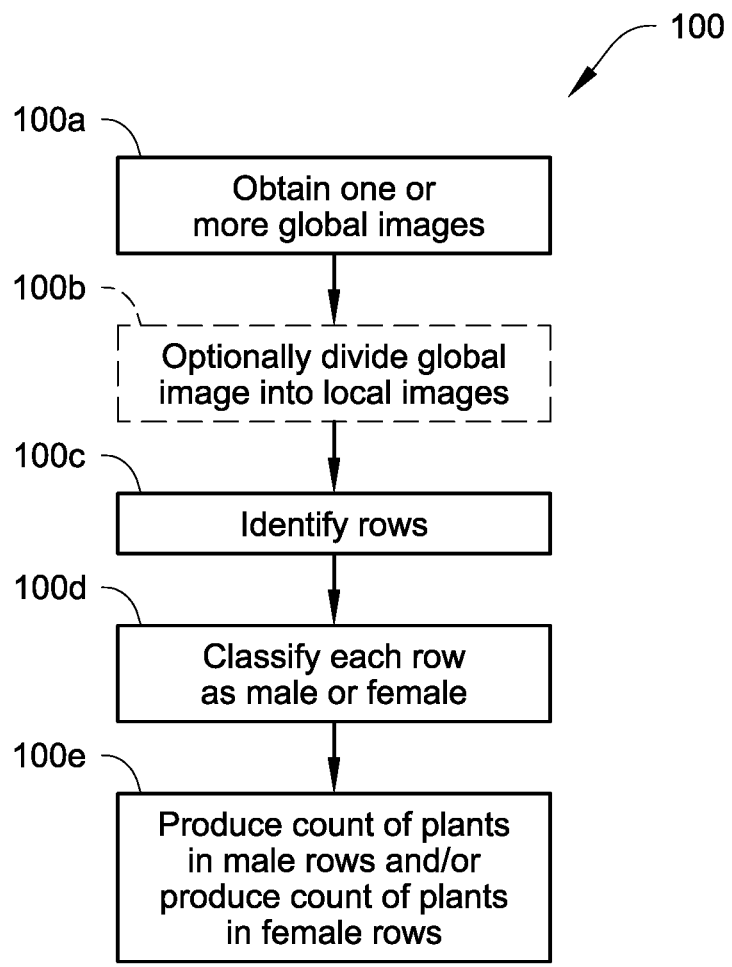

FIG. 8 illustrates an example of a method of seed production plant population counting described herein.

Figure 9:
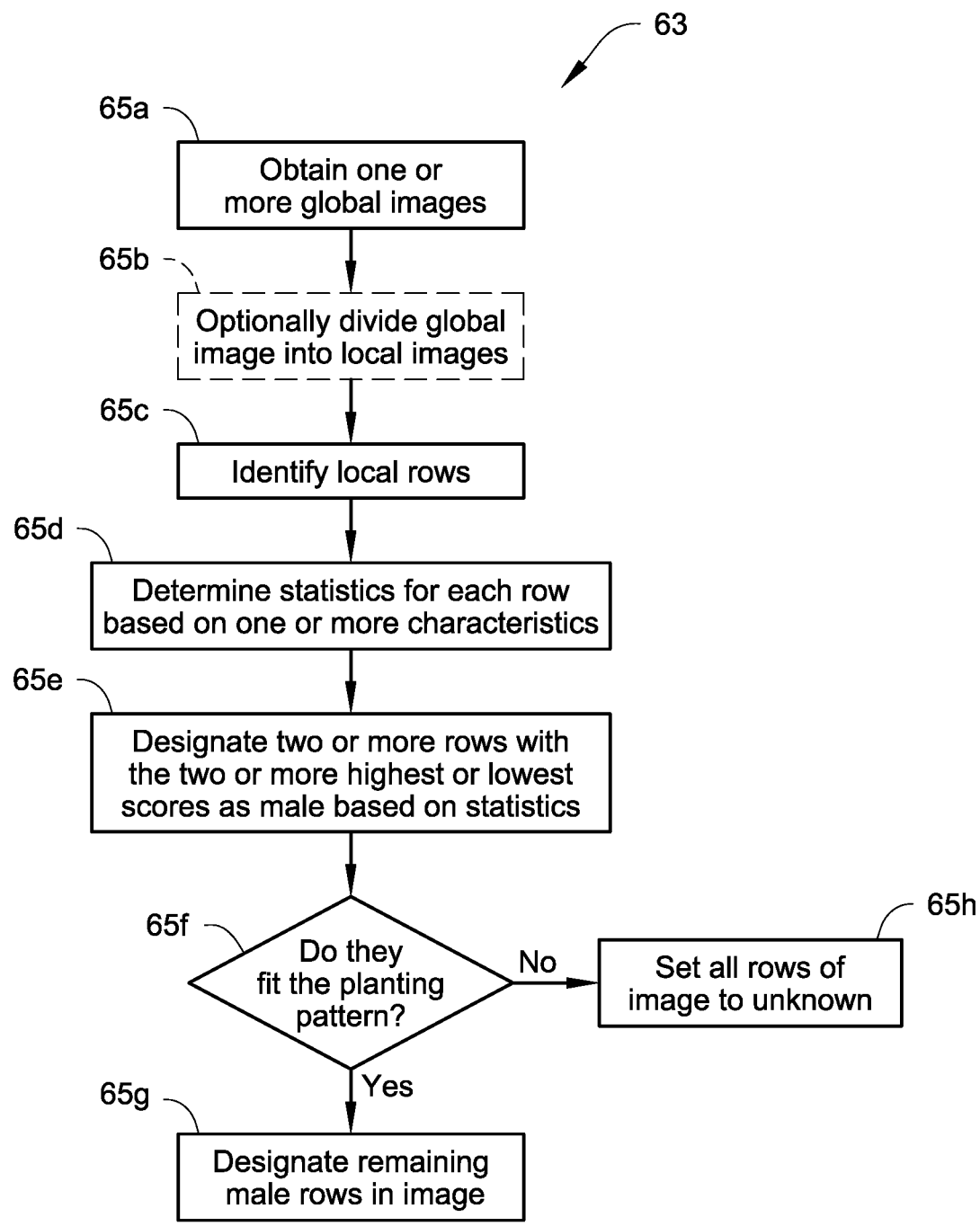

FIG. 9 illustrates an example of an outliers algorithm for classifying plant rows as male or female.

Figure 10:
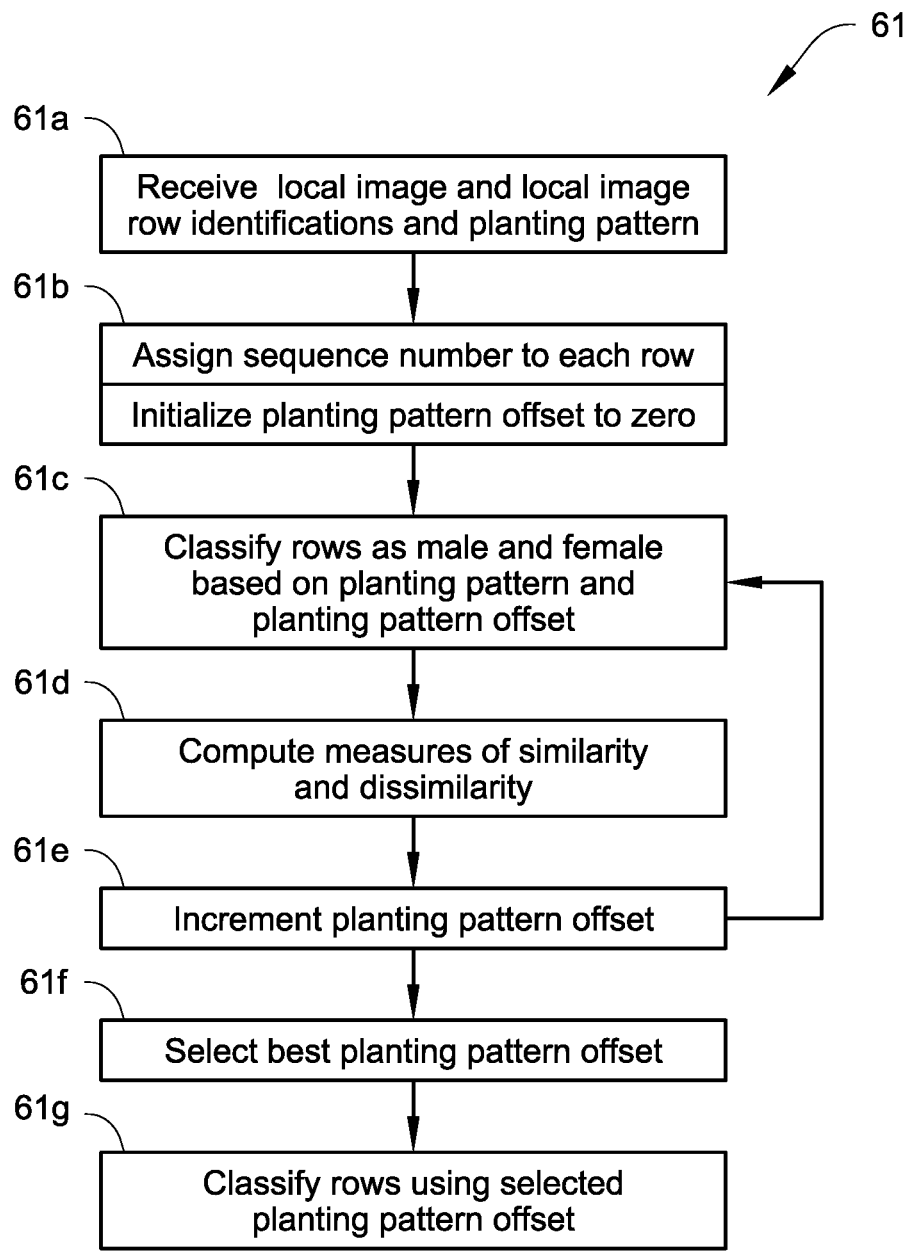

FIG. 10 illustrates a sliding window row classification algorithm.

Figure 11:
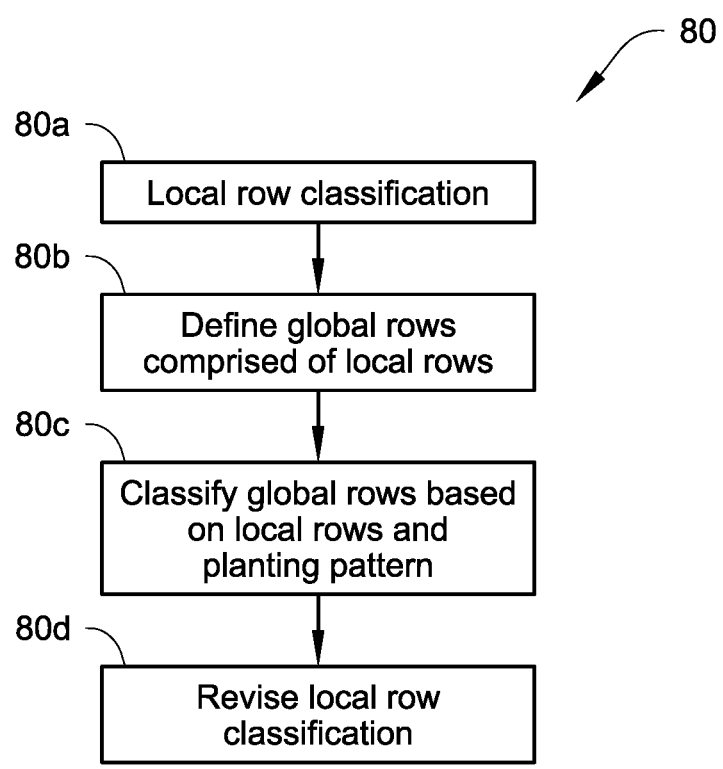

FIG. 11 illustrates a global row analysis algorithm.

Figure 12:
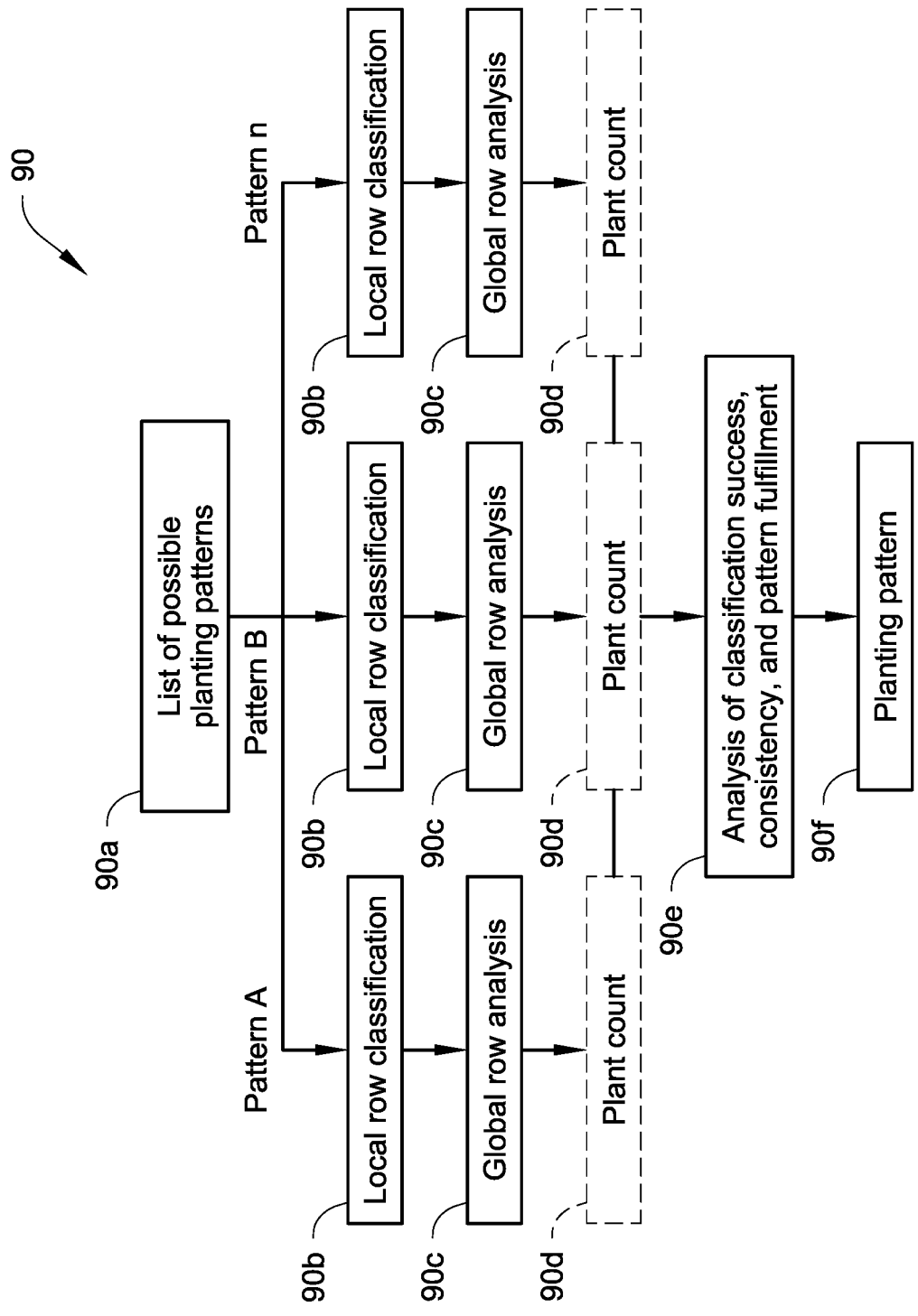

FIG. 12 illustrates a planting pattern detection algorithm.

DETAILED DESCRIPTION

The following is a detailed description of generating population counts for seed production plants based on one or more images obtained from a camera on an aerial vehicle. The aerial vehicle can be an unmanned aerial vehicle such as a UAV or a satellite, or a manned aerial vehicle such as an airplane. As used herein, analyzing an image or performing an analysis on an image is intended to encompass analyzing a global image or a local image. A global image can be a single image of a portion or an entirety of a field where seed production plants are being grown in rows where the single image corresponds to the entire field of view of the camera that obtained the image. A global image can also be a mosaicked image that is derived from two or more images that are mosaicked or combined together to form the global image. A local image is a portion of a global image where the portion is separately analyzed from another portion(s) of the global image. The local image may also be referred to as a sub-image or sub-region of the global image. The term image used by itself herein and in the claims is intended to encompass both a global image and a local image, and the image can be of the entire field or a portion of the field.

The aerial vehicle is flown over a seed production field that includes a plurality of rows of seed production plants. The seed production plants in some of the rows may be referred to as male seed production plants since all of the plants in those rows are intended to be male, while the seed production plants in the other rows may be referred to as female seed production plants since all of the plants in those rows are intended to be female. The aerial vehicle captures one or more images of the seed production field. Analysis is then performed based on the one or more images in order to generate the count of the male seed production plants and/or the count of the female seed production plants. The analysis may optionally include determining which rows of the plants are male plants and which rows are female plants. The image that is analyzed can be a global image or a local image. In one embodiment, some or all of the analysis can occur on the aerial vehicle, for example on one or more processors on a camera mounted on the aerial vehicle. The results of the analysis can then be downloaded from the aerial vehicle or wirelessly transmitted from the aerial vehicle. In another embodiment, the image(s) to be analyzed can be transmitted or downloaded from the aerial vehicle with some or all of the analysis occurring remote from the aerial vehicle.

Figure 1:
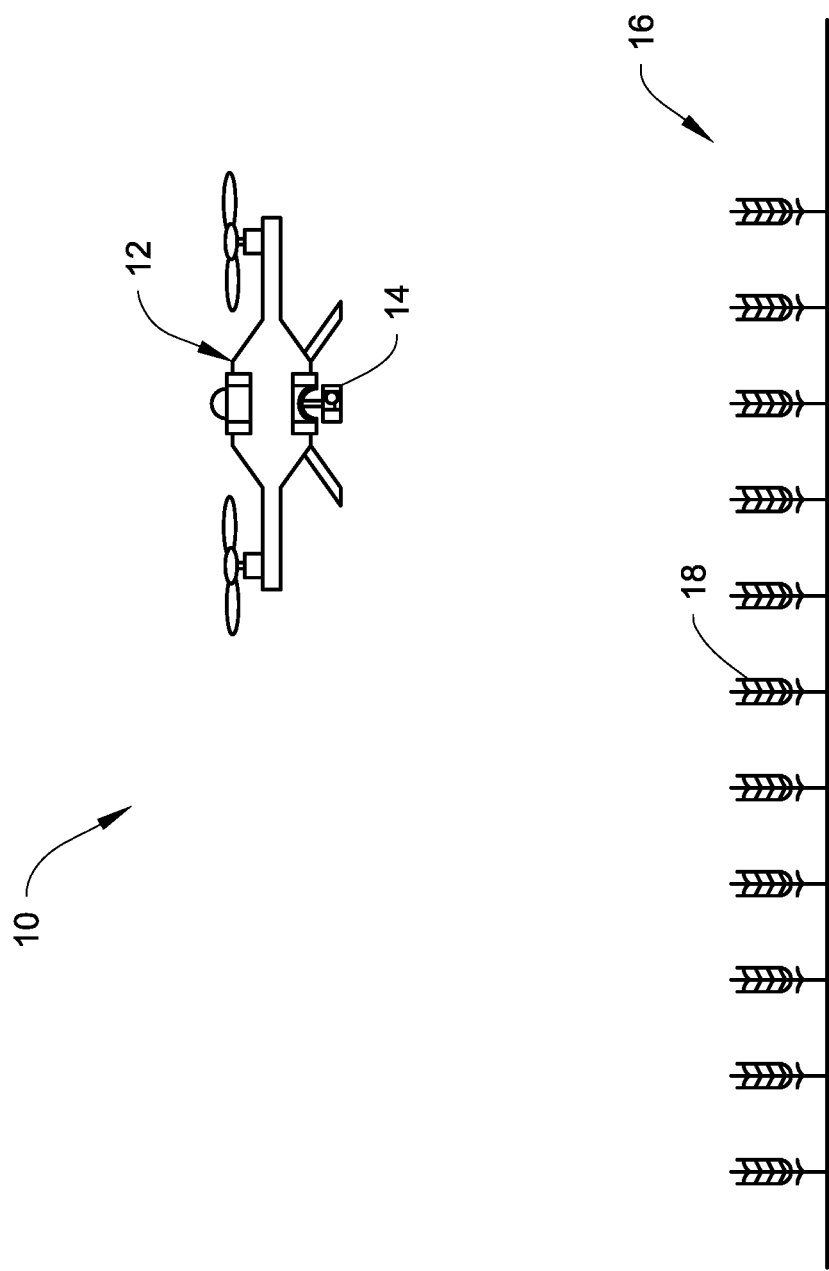

Referring initially to FIG. 1, part of a system 10 described herein is illustrated. The system 10 includes an aerial vehicle 12, in this example depicted as a UAV. In one non-limiting embodiment, the UAV can be a quad-copter or quad-rotor UAV. However, the UAV may alternatively include other types of UAVs including, but not limited to, other type of rotorcraft UAV, a fixed-wing UAV, or another type of UAV. The vehicle 12 includes a camera 14 mounted thereon for capturing images of a seed production field 16 as the vehicle 12 is flown over the field 16. The seed production field 16 includes a plurality of rows of seed production plants 18. The seed production plants 18 can be corn seed plants or any other type of seed production plant in which male and female seed production plants can be distinguished from one another using an aerial image.

In the case of corn seed production, the field 16 is planted with "male" and "female" rows of corn seed production plants. A seed production field will have two different germplasms (i.e. genetic varieties of plant). Pollen from the tassel of the "male" plants fertilizes the silk on the "female" plants to produce seeds with the desired genes. There are several common planting patterns (also called planting configurations). For example:

"4/1" - 4 female plants then 1 male plant in a repeating pattern of 5 rows;
"4/2" - 4 female plants then 2 male plants in a repeating pattern of 6 rows;
"6/1" - 6 female plants then 1 male plant in a repeating pattern of 7 rows.)

Other planting patterns are possible. Planting patterns may have evenly spaced rows or may have unevenly spaced rows.

The rows in an image (global or local) can be numbered sequentially from one side of the image to the other with numeric indices (i.e. 1, 2, 3, 4, 5, 6, ... ). A planting pattern offset is defined as the difference between the numeric index of the first male row and the numeric index of the first row (numeric index of first male row minus numeric index of first row). If row one is male, the planting pattern offset is zero (one minus one). If row two is male, the planting pattern offset is one (two minus one). If row three is the first male, the planting pattern offset is two (three minus one). Planting patterns repeat across a field, so for a given planting pattern there are a finite number of possible planting pattern offsets. For example, in a 4/1 planting pattern, one male row is followed by four female rows, then the pattern repeats. The 4/1 pattern has five elements (one male row and four female rows), so there are five possible planting pattern offsets. If row six is male, then row one is also male, so the planting pattern offset is zero, not five. The classification of all sequential rows in an image is fully defined by the planting pattern (e.g. 4/1) and the planting pattern offset (e.g. 2). A field can have two or more regions, in which case each region may be treated separately. Each region may have its own set of rows, each set of rows numbered sequentially beginning with one. Each region may have a different planting pattern and/or a different planting pattern offset. Regions may be distinguished from each other by a different row direction, or a gap between rows.

Figure 2:
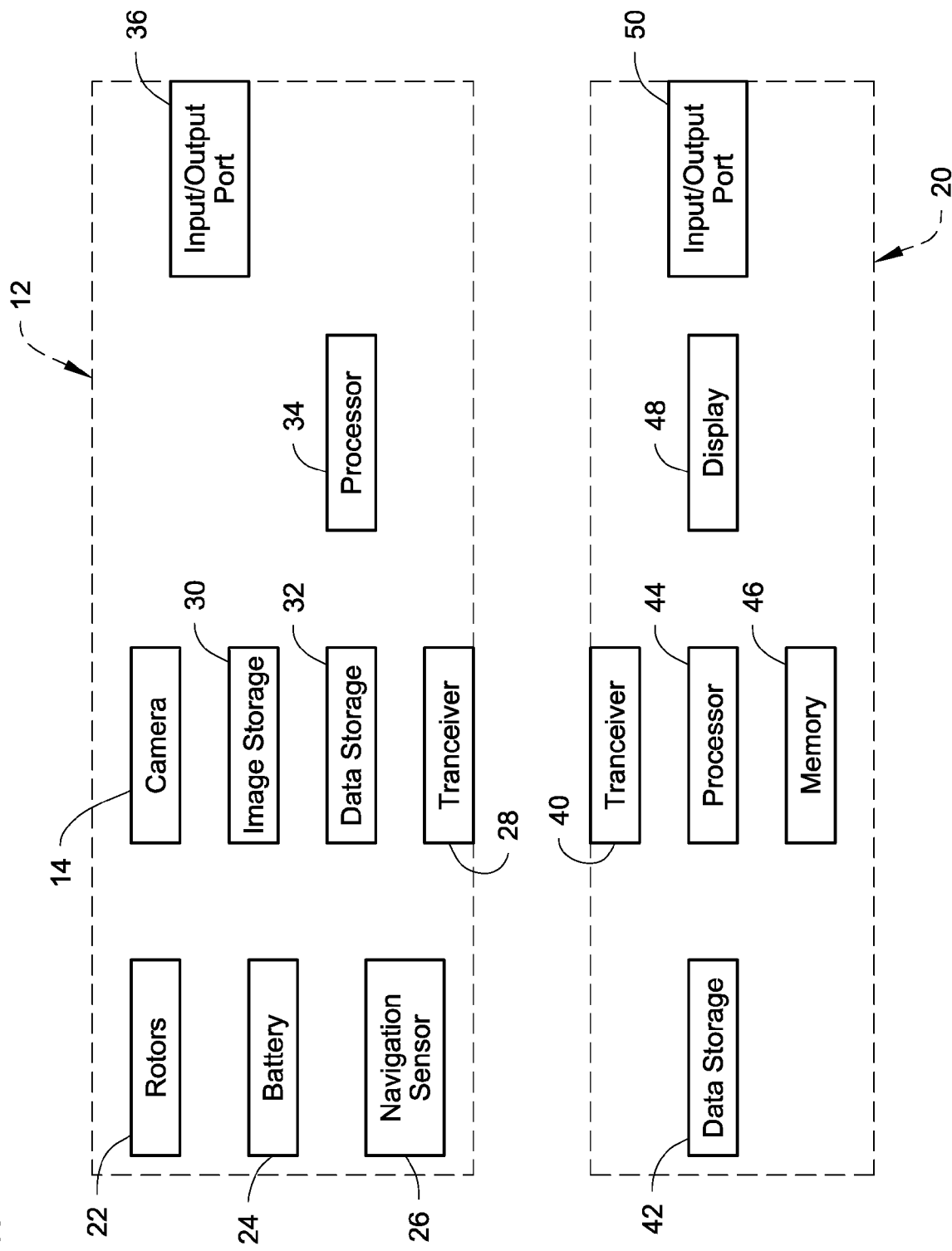

Referring to FIGS. 1 and 2, the system 10 can include the aerial vehicle 12 and a ground control station 20. The vehicle 12 and the station 20 may be in wireless communication with one another using any known conventional wireless communication technique(s). The vehicle 12 can transmit various data to the ground control station 20, for example data obtained from the camera 14. The data transmitted by the vehicle 12 may also be from sensors that sense variables relating to the operation of the vehicle 12, such as navigation sensor data, battery level data and the like. The ground control station 20 can also transmit commands to the vehicle 12. The commands can be, for example, navigational/directional commands, commands to turn on/off various sensors, and other commands.

With continued reference to FIGS. 1 and 2, the vehicle 12 can include the camera 14, one or more rotors or other propulsion mechanisms 22, one or more batteries 24, a navigation sensor 26, and a transceiver 28. The camera 14 can be a conventional camera known in the art for capturing one or more images of the field 16 or portions thereof. The camera 14 can be a gimballed or fixed position video camera. The rotor(s) 22 rotates to provide the lift and propulsion for the vehicle 12. The battery 24, which may be rechargeable, provides stored electrical energy for powering the various electrical components of the vehicle 12. The navigation sensor 26 may include an inertial measurement unit (IMU), which may include an accelerometer and gyroscope to output roll, pitch, yaw, acceleration, or approximate velocity of the vehicle 12 calculated based on acceleration. The navigation sensor 26 may include a compass to provide heading or a global navigation satellite system (GNSS), such as the Global Positioning System (GPS) to provide location. In an example, the navigation sensor 26 may include a tightly coupled IMU and GNSS system, where the IMU data is used to reduce noise in the GNSS positioning accuracy and the GNSS data is used to reduce inertial positioning noise (e.g., drift). The transceiver 28 can be any conventional transceiver known in the art for wirelessly transmitting and receiving data/commands. The camera 14, the one or more rotors 22, the one or more batteries 24, the navigation sensor 26, and the transceiver 28 are each well known in the art.

The vehicle 12 may also optionally include an image storage 30 for storing images obtained by the camera 14, a data storage 32 for storing other data, one or more processors 34 (for example a CPU or GPU or FPGA) that can process images and/or data on the vehicle 12, and an input/output port 36 that can mechanically interface with a suitable mechanical connector for transferring data from or into the vehicle 12. In some embodiments, the image storage 30 and the data storage 32 can be combined into a single storage device.

With continued reference to FIGS. 1-2, the ground control station 20 can include a transceiver 40, a data storage 42, one or more data processors 44, a memory 46 that stores data processing algorithms, a display screen 48, and an input/output port 50. Other elements can also be included on the ground control station 20 such as one or more user inputs which can be, for example, input buttons or inputs on a touchscreen which can be separate from, or incorporated into, the display screen 48. The transceiver 40 can be any conventional transceiver known in the art for wirelessly communicating with the vehicle 12. The data storage 42 can store data, such as image data received from the vehicle 12. The one or more processors 44 can be, for example, a CPU or GPU or a FPGA, that can process images and/or data obtained by the vehicle 12. The display 48 can display one or more images obtained by the vehicle 12 and/or display a map, such as a zone map or a point map, generated from the image(s) obtained by the vehicle 12. The input/output port 50 can mechanically interface with a suitable mechanical connector for transferring data from or into the station 20.

Figure 3:
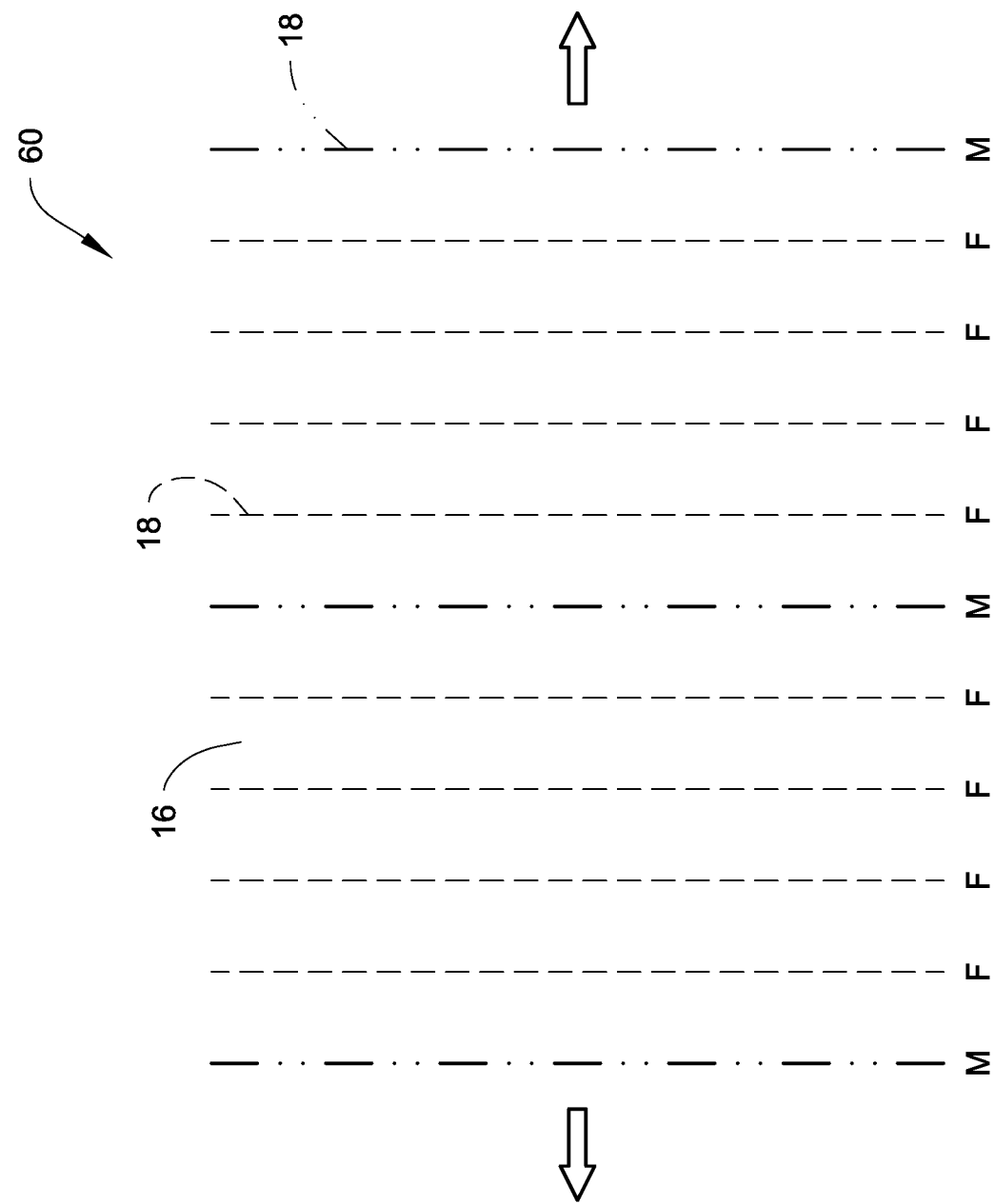
FIG. 3 is a top view of a seed production field with one example of a planting pattern.

FIG. 3 is a schematic depiction of an image 60 of the seed production field 16 obtained by the camera of the vehicle. The image 60 can be an image corresponding to the field of view of the camera. In another embodiment, the image 60 could be a mosaic image generated by aggregating a set of images from the camera using a stitching process known in the art. The image 60 may also be a local image (i.e. a sub-image) which is a region of the seed production field that is extracted from a larger image so that the local image is smaller in coverage area of the seed production field than the image it is extracted from. The image 60 may be georeferenced to have a defined location, orientation, and size that enables association of any pixel of the image 60 with a point or area on or near the surface of earth. Commonly, the top left pixel is defined with a latitude/longitude or Universal Transverse Mercator (UTM) X/Y, and each pixel has a defined X and Y size, which are often the same.

The image 60 depicts the seed production field 16 as having a 4/1 planting pattern of the plants 18, with continuing sequences of 1 male (M) row (i.e. a row of male seed production plants) and 4 female (F) rows (i.e. rows of female seed production plants). Image processing can be performed on the image 60 to generate one or more plant counts. The plant count(s) can then be stored on a tangible computer-accessible storage medium. The plant count can be, but is not limited to, an absolute count of the total number of plants in the field, the number of seed production plants in the male rows and the number of seed production plants in the female rows, a density of the plants (for example, a number of male seed production plants per acre and/or a number of female seed production plants per acre), a percentage of a row (e.g. a percentage of a row, whether male or female, that is or is not covered by seed production plants), a percentage of rows within an area or region (e.g. a percentage of the total length of male rows that are or are not covered by seed production plants and/or a percentage of the total length of female rows that are or are not covered by seed production plants), or a percentage of an area or region (e.g. a percentage of an area or region that is or is not covered by male and/or female seed production plants).

During the analysis to produce the plant count, it may be necessary to identify the plurality of rows of seed production plants, i.e. where is each row regardless of whether the row includes male or female seed production plants. In addition, it may be necessary to classify each one of the identified rows as either male or female. The classification as male or female can be based on a priori knowledge of the planting pattern in the field, or the planting pattern may need to be determined.

Figure 4:
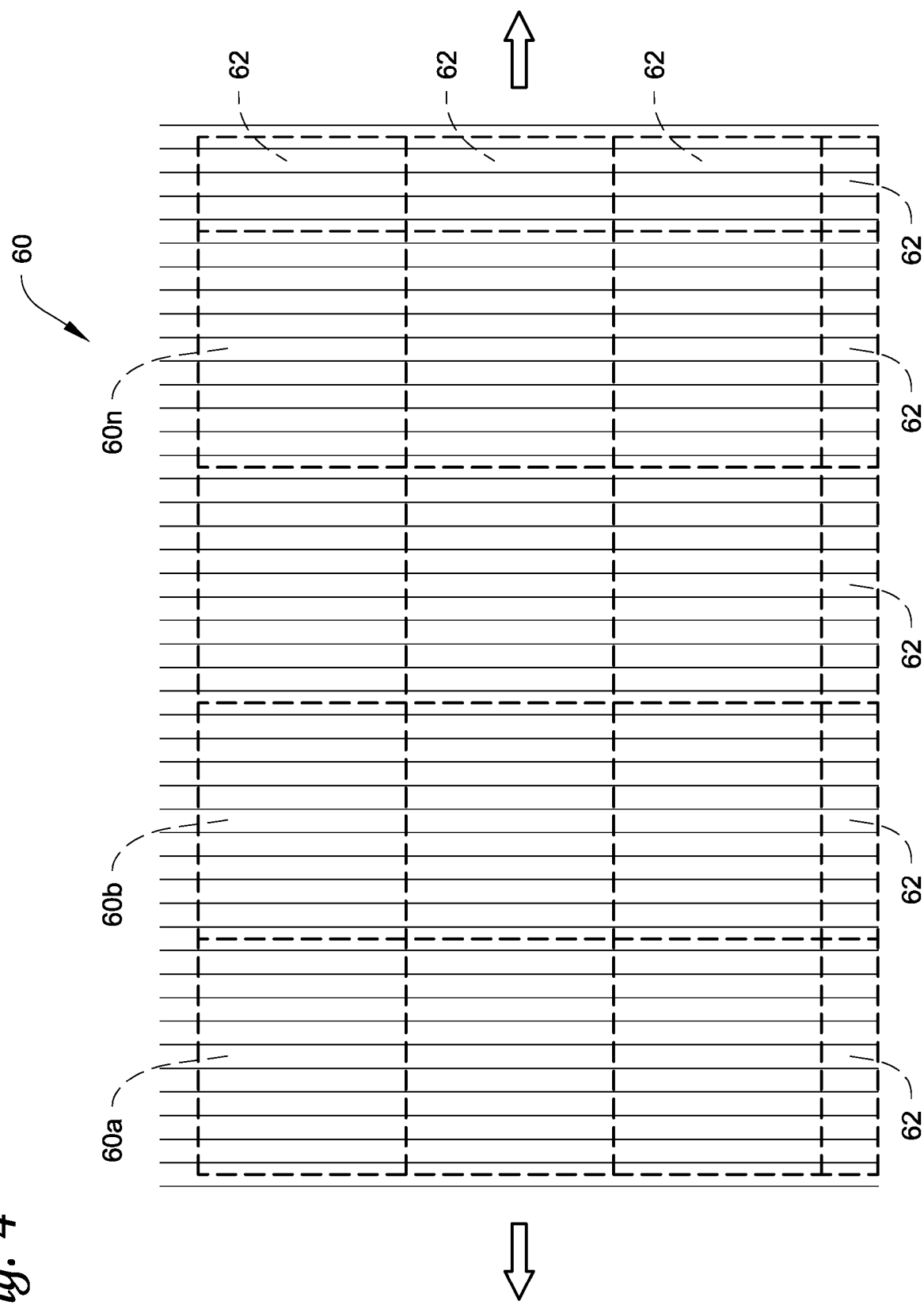
FIG. 4 depicts an image of the seed production field divided into local images.

Referring to FIG. 4, the image 60, in this case a global image, may be divided into a plurality of local images 60a, 60b,...n. The local images 60a, 60b,...n can be squares, rectangles or other polygons. The local images 60a, 60b,...n can be obtained by dividing the image 60 into equally sized polygons such as rectangles. Alternatively, the size of the local images can be based on row width. For example, the image 60 can be divided into local images of approximately 12 crop rows. If the approximate or exact ground sample distance is known (length of the side of one pixel in the image, e.g. 0.2″), and the distance between crop rows is known (e.g. 30″), to extract local images of approximately 12 crop rows, the local image size may be set to 12 rows × 30″ per row / 0.2″ per pixel = 1800 pixels. The local images could have any number of crop rows, for example from 4 rows to 30 rows. Another technique to form the local images is to divide the image 60 into approximate areas regardless of crop row width. In addition, the image 60 can be divided into arbitrary sizes in pixels without regard for row width or area.

As depicted in FIG. 4, local images 62 near one or more edges of the image 60 may not form the desired local image size, i.e. the size of the local images 62 may not match the size of the local images 60a, 60b...60n. In these cases the improperly sized local images 62 can be handled in a number of ways. For example, the local image 62 can be made larger to make the local image 62 part of an adjacent local image 60. Another option is to treat the smaller local image 62 as a regular local image 60. Another option is to exclude the local images 62 from the processing (i.e. discard the local images 62 from the processing).

As indicated above, part of the plant counting may require classifying the rows as male or female. Any technique for identifying or classifying the rows as male or female can be used. The classification process may utilize one or more images (e.g. a global image or a local image) obtained by the vehicle.

Figure 5:
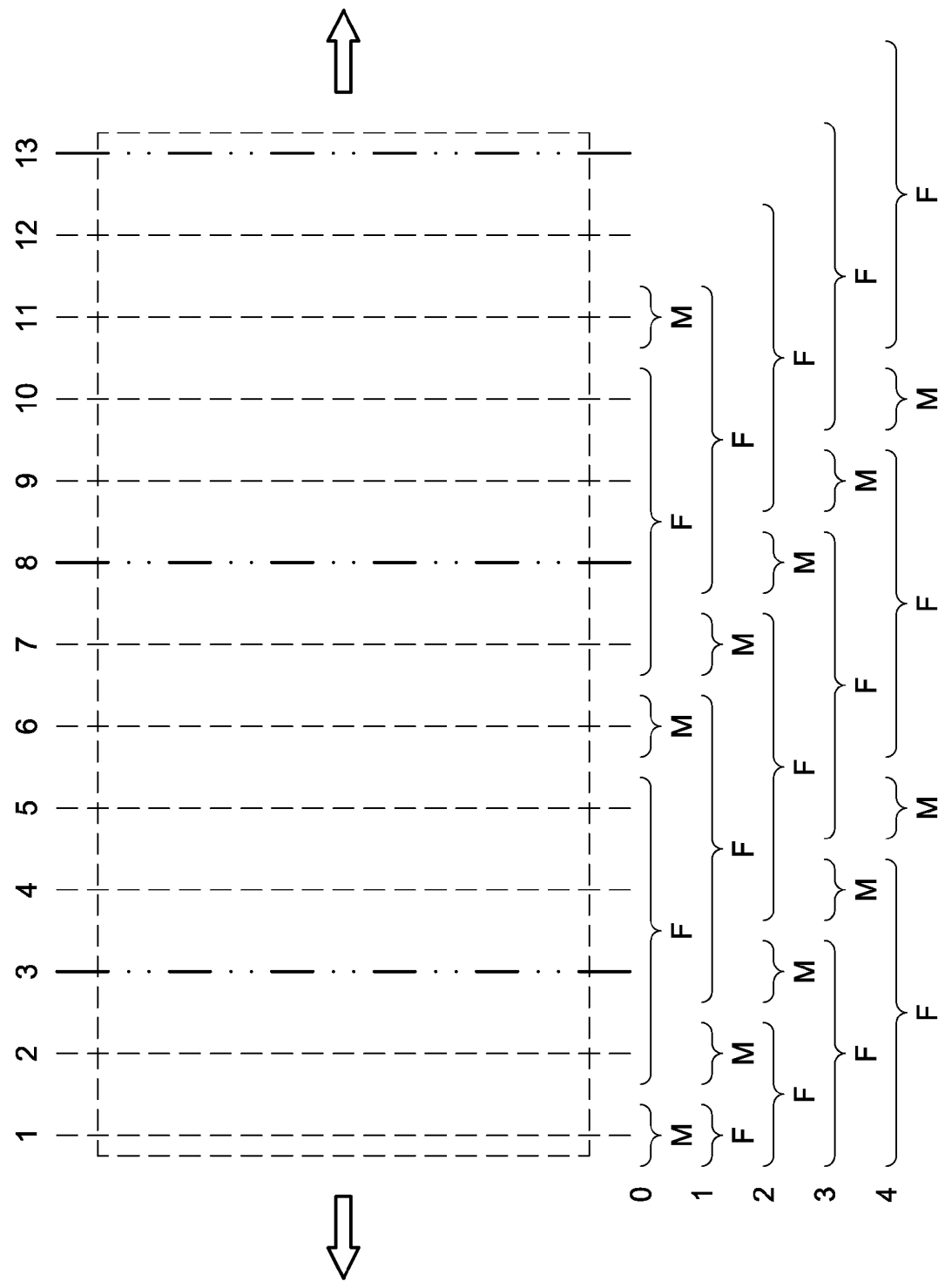
FIG. 5 depicts the concept of a sliding window row classification algorithm.

FIGS. 5 and 10 illustrate one classification technique which may be referred to as a sliding window row classification algorithm 61. This technique is useful in instances where the planting pattern is known. For example, in a 4/1 pattern illustrated in FIG. 5, once an image, for example a local image, the local image row identifications (see step 100c in FIG. 8) and the planting pattern are received at step 61a each row is assigned a number in step 61b. In addition, the planting pattern offset is set to zero (i.e. see the 0 offset line in FIG. 5 where rows 1, 6, 11 and 16 are assumed to be male and the other rows in FIG. 5 are assumed to be female; in the next offset line 1, rows 2, 7, and 12 are assumed to be male and the other rows are assumed to be female; etc.). Then, in step 61d, a measure of similarity among male rows is computed as well as computing a measure of similarity among the female rows. In addition, in step 61d, a measure of dissimilarity between the set of male rows and female rows is computed. Examples of similarities and dissimilarities are explained in FIGS. 7A-G. The measures of similarity and dissimilarity can be based on, but not limited to, range (maximum minus minimum), standard deviation, Euclidean distance, or Minkowski distance. In a second step (see offset line 1), the window is slid to the right by 1 (i.e. the planting pattern offset is set to 1 instead of 0), where now rows 2, 7, and 12 are assumed to be male, and the other rows are assumed to be female, and the computation of measurements of similarity and dissimilarity is repeated. This process is repeated, for example 5 times, covering every possible offset of the first male row in the image. Thereafter, the offset that produces the highest similarity among rows of one gender and the highest dissimilarity between the set of rows corresponding to each gender is selected at step 61f. If the planting pattern is not known, all known planting patterns can be tried and the planting pattern with the most consistency among rows within genders and the most dissimilarity between rows of opposite genders can be selected.

FIG. 9 illustrates another classification technique which may be referred to as an outliers row classification algorithm 63. This algorithm 63 is also useful when the planting pattern is known. In this algorithm, one or more images are received at step 65a and optionally divided into local images in an optional step 65b such that at least two male rows are present in each local image. The rows in one of the local images are then identified at step 65c, and statistics (for example, mean, maximum, minimum, mean after removing outliers, standard deviation, etc.) of one or more characteristics (discussed below with respect to FIGS. 7A-G) for each row are calculated at step 65d. Thereafter, two rows in the local image that are probably male are identified at step 65e by finding the two rows that are the most different from the other rows using one or more identifying characteristics (e.g. the two thickest rows). A check is then performed at step 65f to determine if the two identified male rows satisfy the planting pattern (e.g. they are five rows apart in a 4/1 female-male planting pattern). If the identified male rows satisfy the planting pattern, the remaining males in the local image are found at step 65g by counting forward and backwards from one of the males based on the planting pattern. Any row in the local image that is not male is classified as female. Male and female rows in the local image are added to their respective lists of known male and female rows for the global image. If the two identified male rows do not satisfy the planting pattern, the local image can be skipped and all the rows in the local image are added to a list of unclassified rows for the local image at step 65h.

Variations of the technique in FIG. 9 are possible. For example, one can look for "N" male row candidates, where N is the expected number of male rows based on the planting pattern and local image size, or lower than the expected number. Male plants may not always be the "thickest", and in some cases they may be the thinnest. Therefore, one can find the two rows with the highest values for a particular plant/row characteristic and the two rows with the lowest values for a particular plant/row characteristic. Then both pairs can be compared against the planting pattern. In some cases, it may be very difficult to classify rows as male and female. In these cases, more than one plant/row characteristic may be used. In these cases, several independent records of row gender classification may be generated for each local image. Then, a global row analysis, described below, may consider consistency of classification along rows spanning multiple local images, and fulfillment of the planting pattern over the sequence of rows. Final gender classification may be based on one or more plant/row characteristics providing maximum consistency. In some cases, a combination of characteristics may be used during the global row analysis. For example, it's possible many local images may succeed in classification based on row thickness while other local images may succeed in classification based on plant color. It's also possible that local image classification itself could use multiple characteristics.

Referring to FIGS. 7A-G, additional examples of classifying the rows as male or female are depicted based on identifying one or more characteristic of each row. Characteristics can include, but are not limited to, plant color (RGB); multispectral characteristics (for example, NDVI, NDRE, or narrow band reflectance or irradiance); differences in plant height (e.g. male and female plants have different heights); plant size (height, area (as projected in a 2D image), distance (which could be length of one side of a rectangle containing the plant, or the diameter of a circumscribed circle, or maximum distance between two points); row vegetation width (i.e. a distance perpendicular to the row), especially when the plants are big; individual plant size; variability in plant size (sometimes male plants are planted on different days, in a row offset by a couple inches); plant closeness to row center (sometimes male plants are planted on different days, in a row offset by a couple inches); plant spacing (a.k.a. seeding rate, plant density, plant linear density); variability in plant spacing (e.g. when male plants are planted on different days, their spacing may be less even than female plant rows); offset of row relative to neighboring rows (e.g. four rows are evenly spaced, fifth row is slightly offset as a result of separate, slightly misaligned planting); planting date information for both female rows and male rows; expected growth rate for both female plant varieties and male plant varieties; number of leaf tips; etc.

FIG. 7A illustrates an example of male/female classification using plant color. Color can be, but is not limited to, red, green, blue (RGB); a monochromatic color; an index that is computed from one or more colors, such as excess green. The classification may also be based on multispectral bands or indices including wavelengths of light not visible to the human eye such as near infrared and red edge. In FIG. 7A, the plants in the row 70a (which could be a male row or a female row) have a different color than the plants in the row 70b (which could be male or female) as indicated by the different hatching in the circles each circle indicating a discrete plant.

FIG. 7B illustrates an example of male/female classification using plant size. In FIG. 7B, the plants in the row 70c (which could be a male row or a female row) have a different, larger size than the plants in the row 70d (which could be male or female) as indicated by the different diameters of the circles each circle indicating a discrete plant.

FIG. 7C illustrates an example of male/female classification using row width. In FIG. 7C, the row 70e (which could be a male row or a female row) has a different, larger width (i.e. represented by the distance between the two lines in the row) than the row 70*f* (which could be male or female) with the vertical lines in each row indicating the approximate maximum or average width of the plants in each row.

FIGS. 7D-1 and 7D-2 illustrate examples of male/female classification based on variations in plant size and plant closeness to row center. In FIG. 7D-1, the plants in the row 70*g* (which is indicated as being a male row) have generally the same size and they may be larger than the plants in the row 70*h* which is indicated as being a female row. In addition, the plants in the row 70*g* have variations in distance to the center of the row (i.e. some of the plants in the row 70*g* are offset from the center of the row), while the plants in the row 70*h* have consistent distance to the row center. In FIG. 7D-2, some of the plants in the row 70*g* have different sizes than other plants in the row 70*g*, and the plants in the row 70*g* are aligned (i.e. not offset) on the row center.

FIG. 7E illustrates an example of male/female classification based upon plant spacing in the rows. In FIG. 7E, the plants in the row 70*i* (which could be a male row or a female row) have a first spacing between each plant, while the plants in the row 70*j* (which could be male or female) have a second spacing that is different than the spacing in the row 70*i*.

FIG. 7F illustrates an example of male/female classification based upon variability in plant spacing in the rows. In FIG. 7F, the plants in the row 70*k* (which could be a male row or a female row) have a variable spacing between some or all of the plants, while the plants in the row 70*l* (which could be male or female) have a consistent spacing between the plants in the row 70*l*.

FIG. 7G illustrates an example of male/female classification based upon variability in row spacing. In FIG. 7G, there is a difference in spacing 72 between the male rows 70*m*, 70*n* and their adjacent female rows that is different than the spacing 74 between the female rows.

Figure 6:
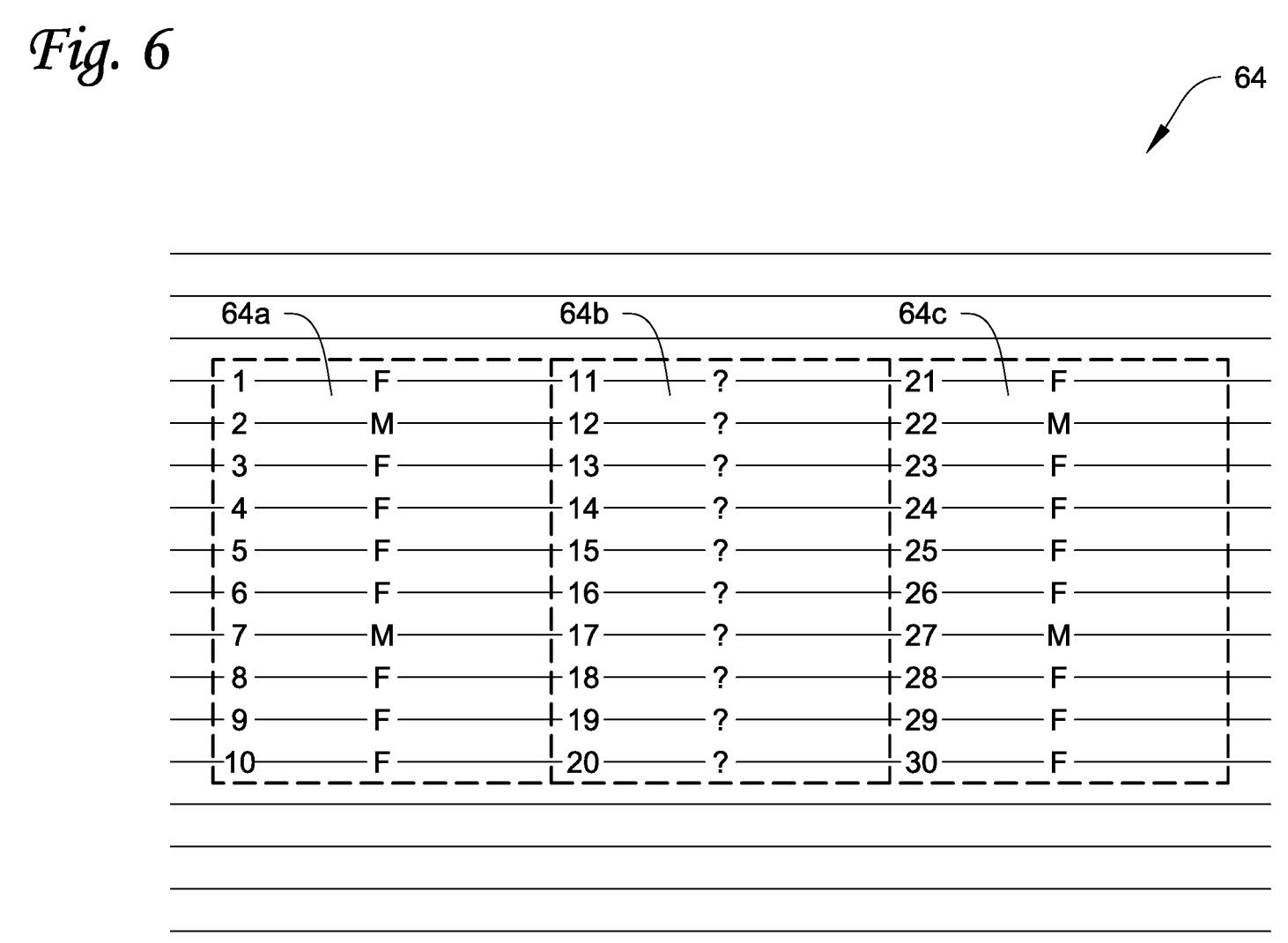

As described above, a global row analysis may be employed to consider consistency of classification among the local rows, and fulfillment of the planting pattern over the sequence of the local rows. A local row is a row that is within a local image. A global row is a row that extends across two or more local images and is comprised of two or more local rows. FIG. 6 illustrates a global image 64 that is divided into local images 64*a*, 64*b*, 64*c*. Each local image 64*a-c* includes local rows (local rows 1-10 in 64*a*; local rows 11-20 in 64*b*; local rows 21-30 in 64*c*). The local rows 1, 11, 21 form a global row; the local rows 2, 12, 22 form a global row; etc. In the example in FIG. 6, there are two male rows with the rest being female rows.

FIG. 11 depicts an example of the global row analysis algorithm 80. The global row analysis algorithm 80 may be employed when gender classification fails on some local images resulting in unclassified local rows. For example, FIG. 6 illustrates the local image 64*b* with unclassified local rows 11-20. In addition, gender classification may be complete on some local images, but provide incorrect results. The following algorithm addresses both issues, and may be applied subsequent to either the sliding window row classification algorithm or the outliers row classification algorithm.

Referring to FIGS. 6 and 11, once the local rows are classified at step 80*a*, the local rows in the image (male, female, and unclassified) are clustered into the same global row at step 80*b* by checking if they connect between the local images 64*a*, 64*b*, 64*c*. Each global row is then classified at step 80*c* as male or female based on one or more of: 1) a vote of classification of associated local rows; and/or 2) fulfillment of the planting pattern. Once a global row is assigned a gender, all local rows in that global row will receive its gender classification. In FIG. 6, local rows 1-10 are classified in local image 64*a*. In local image 64*b*, the local rows 11-20 cannot be classified. Local rows 21-30 are classified in local image 64*c*. Local row 11 is classified as female because the majority of local rows in the corresponding global row are female. Local row 12 is classified as male because the majority of local rows in the corresponding global row are male.

In cases where nearly all local rows of a global row are classified as male, but a few local rows are unclassified, the global row is classified as male. In cases where nearly all local rows are classified as male, but a few local rows are classified as female, the global row is classified as male. In cases where a similar number of local rows are classified as male as are classified as female, the global row may be classified based on planting pattern. The exact formula for weighting planting pattern and local row classification could take many forms. For example, global rows with unanimous agreement, or high agreement may be classified first and used to determine the planting pattern offset. Global rows or local rows which don't fit the planting pattern are flagged for further review.

In situations where the planting pattern in the field is not known, a planting pattern detection algorithm can be implemented in order to determine the planting pattern. One example of a planting pattern detection algorithm 90 is illustrated in FIG. 12. Starting with each possible planting pattern at step 90*a*, a local row classification algorithm (e.g. sliding window algorithm 61, outliers algorithm 63, or other) is run at step 90*b* for each possible planting pattern. In addition, the global row analysis algorithm 80 is separately run on the results for each planting pattern at step 90*c*. Optionally, the plant count 90*d* can be determined after the global row analysis 90*c*. Measures of classification success, consistency and planting pattern fulfillment from the global row analysis and the plant count are saved at step 90*e*. These include counts of classified vs. unclassified rows in the local image(s); counts of discrepancies between local rows and global rows; and counts of global rows whose classification does not fit the planting pattern. The planting pattern that produces the best measures of classification success, consistency, and pattern fulfillment is selected as the planting pattern at step 90*f*. In some embodiments, the planting pattern detection algorithm 90 could be run on a single local image or a global image, a plurality of local images or global images, or a subset of local images or global images to save time. In addition, the planting pattern detection algorithm 90 could be run first, then after determining the planting pattern, the row classification, global row analysis and the option plant count could be run from the beginning with the determined planting pattern. In addition, the planting pattern detection algorithm 90 could be run first, and results for all planting patterns saved. Upon determining the "winning" planting pattern, results from all other planting patterns could be discarded and the results of the winning planting pattern can be output. In addition, the planting pattern detection algorithm 90 could be run first, without optional plant count step 90*d*. Upon determining the "winning" planting pattern, the plant count step 90*d* may be performed using data generated from steps 90*b* and 90*c* of the "winning" planting pattern.

Referring to FIG. 8, a method 100 of seed production plant population counting in a seed production field that includes a plurality of rows of seed production plants is illustrated. The method 100 includes receiving one or more global images at step 100*a*. The global image(s) may then optionally be subdivided into local images at step 100*b* as described above. The rows (whether global rows or local rows) of plants in the image (whether a global image or a local image) are then identified at step 100*c*. Techniques for identifying plant rows are known in the art. Thereafter, each row is classified as either male or female in step 100*d*, for example using one of the classification techniques described above. Then, at step 100*e*, a count is produced for the male plants and the female plants. At the time of filing this application, suitable techniques for counting plants are known in the art. In some embodiments, only a male plant count can be produced or only a female plant count can be produced.

Once the plant count(s) is produced, an estimated seed yield can be generated. Techniques for estimating yield using plant count (also called stand count) are known in the art.

In addition to generating plant counts, additional possible outputs using the data can include:

Vector data layer
- A set of geolocations, each geolocation being a single point (i.e. a point vector data layer) or a polygon (i.e. a polygon vector data layer), and each geolocation being associated with one or more data values (e.g. male stand count and female stand count).
- In a point vector data layer, geolocations can be random, an imperfect grid, or a perfect grid.
- In a polygon vector data layer, the geolocations can define regular polygon shapes or irregular shapes.
- Often saved as an "ESRI Shapefile", GeoJSON, GeoPackage, Spreadsheet, CSV (comma separated value), or text file.

Raster data layer
- A perfect grid of geolocations, each geolocation being a single point or a single rectangular area (also known as a cell), and each geolocation being associated with one or more data values (e.g. male stand count and female stand count).
- Often saved as a GeoTIFF.

Spot map
- A visualization of the point vector data layer.

Zone map
- A visualization of a polygon vector data layer.

Heat map
- A visualization of the raster data layer.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of hybrid corn seed production plant population counting in a hybrid corn seed production field that includes a plurality of rows of hybrid corn seed production plants, comprising:
   receiving a plurality of aerial images of the hybrid corn seed production field, the aerial images being obtained by a camera on an unmanned aerial vehicle that is flown over the hybrid corn seed production field;
   processing the aerial images using one or more computer processors, with the one or more computer processors:
   a) for each one of the aerial images, identifying the plurality of rows of hybrid corn seed production plants;
   b) for each one of the aerial images, classifying each one of the identified rows of hybrid corn seed production plants as either male or female; and
   c) for each one of the aerial images, producing a count of the number of hybrid corn seed production plants in the male rows or producing a count of the number of hybrid corn seed production plants in the female rows;
   storing the counts produced in c) on a tangible computer-accessible storage medium;
   wherein prior to classifying each one of the identified rows of hybrid corn seed production plants, analyzing each one of the aerial images to identify one or more physical characteristics of the hybrid corn seed production plants in each row and/or analyzing each one of the aerial images to identify one or more physical characteristics of each row of the hybrid corn seed production plants; and
   classifying each one of the identified rows of hybrid corn seed production plants as either male or female based on the one or more identified physical characteristics of the hybrid corn seed production plants in each row and/or based on the one or more identified physical characteristics of each row of the hybrid corn seed production plants.

2. The method of claim 1, further comprising producing a map of the hybrid corn seed production field using the counts produced in c).

3. The method of claim 1, wherein the aerial images are global images or local images.

4. The method of claim 1, further comprising associating a geolocation with each one of the aerial images, wherein the geolocations are determined by a navigation sensor of the unmanned aerial vehicle.

5. The method of claim 1, comprising transferring the aerial images from the unmanned aerial vehicle to a separate location, and performing a)-c) at the remote location.

6. The method of claim 5, wherein the separate location is a ground control station.

7. The method of claim 1, wherein a)-c) are performed on the unmanned aerial vehicle in real-time while the unmanned aerial vehicle is in flight.

8. The method of claim 1, wherein c) comprises producing counts of the number of hybrid corn seed production plants in the male rows and producing counts of the number of hybrid corn seed production plants in the female rows; and storing the counts on the tangible computer-accessible storage medium.

9. The method of claim 1, comprising associating each one of the counts produced in c) with a corresponding geolocation; producing a spot map, a zone map, or a heat map using the geolocations; and displaying the spot map, the zone map or the heat map on a display.

10. The method of claim 1, further comprising using the counts produced in c) to estimate hybrid corn seed yield.

11. The method of claim 1, comprising producing a spot map, and saving the geolocations and the counts as a vector data layer file.

12. The method of claim 1, wherein the physical characteristics comprise one or more of plant color, plant size and plant spacing.

13. A system of hybrid corn seed production plant population counting in a hybrid corn seed production field that includes a plurality of rows of hybrid corn seed production plants, comprising:
   an unmanned aerial vehicle having at least one camera to obtain aerial images of the hybrid corn seed production field;
   a tangible computer-accessible storage medium on the unmanned aerial vehicle that stores the aerial images of the hybrid corn seed production field obtained by the at least one camera;
   a processor to:

a) use the aerial images to identify the plurality of rows of hybrid corn seed production plants in the aerial images;

b) for each one of the aerial images, analyzing each one of the aerial images to identify one or more physical characteristics of the hybrid corn seed production plants in each row and/or analyzing each one of the aerial images to identify one or more physical characteristics of each row of the hybrid corn seed production plants;

c) for each one of the aerial images, classify each one of the identified rows of hybrid corn seed production plants as either male or female based on the one or more identified physical characteristics of the hybrid corn seed production plants in each row and/or based on the one or more identified physical characteristics of each row of the hybrid corn seed production plants; and d) for each one of the aerial images, produce a count of the number of hybrid corn seed production plants in the male rows or produce a count of the number of hybrid corn seed production plants in the female rows.

14. The system of claim 13, wherein the processor produces a map of the hybrid corn seed production field using the counts produced in d).

15. The system of claim 13, wherein the aerial images are global images or local images.

16. The system of claim 13, wherein the processor is separate from the unmanned aerial vehicle.

17. The system of claim 13, wherein the processor is on the unmanned aerial vehicle.

18. The system of claim 13, wherein for each one of the aerial images, the processor produces a count of the number of hybrid corn seed production plants in the male rows and produces a count of the number of hybrid corn seed production plants in the female rows.

19. A method of hybrid corn seed production plant population counting in a hybrid corn seed production field that includes a plurality of rows of male and female hybrid corn seed production plants, comprising:

flying an unmanned aerial vehicle over the hybrid corn seed production field;

capturing aerial images of the hybrid corn seed production field using a camera on the unmanned aerial vehicle as the unmanned aerial vehicle is flown over the hybrid corn seed production field and storing the aerial images;

processing the aerial images using one or more computer processors to produce, for each one of the aerial images, a count of the number of male hybrid corn seed production plants or produce a count of the number of female hybrid corn seed production plants;

storing the counts on a tangible computer-accessible storage medium;

wherein processing the aerial images includes for each one of the aerial images:

a) identifying the plurality of rows of male and female hybrid corn seed production plants;

b) for each one of the aerial images, analyzing each one of the aerial images to identify one or more physical characteristics of the hybrid corn seed production plants in each row and/or analyzing each one of the aerial images to identify one or more physical characteristics of each row of the hybrid corn seed production plants;

c) classifying each one of the identified rows as either male or female based on the one or more identified physical characteristics of the hybrid corn seed production plants in each row and/or based on the one or more identified physical characteristics of each row of the hybrid corn seed production plants;

d) producing the count of the number of male hybrid corn seed production plants in the identified male rows or produce the count of the number of female hybrid corn seed production plants in the identified female rows.

20. The method of claim 19, comprising processing the aerial images to, for each one of the aerial images, produce a count of the number of male hybrid corn seed production plants and produce a count of the number of female hybrid corn seed production plants; and storing the counts on the tangible computer-accessible storage medium.

21. A method of hybrid corn seed production plant population counting in a hybrid corn seed production field that includes a plurality of rows of hybrid corn seed production plants, comprising:

collecting a plurality of aerial images of the hybrid corn seed production field using a camera on an unmanned aerial vehicle that is flown over the hybrid corn seed production field;

transferring the aerial images from the unmanned aerial vehicle to a ground control station;

processing the aerial images in the ground control station using one or more computer processors of the ground control station, with the one or more computer processors:

a) for each one of the aerial images, identifying the plurality of rows of hybrid corn seed production plants;

b) for each one of the aerial images, classifying each one of the identified rows of hybrid corn seed production plants as either male or female; and c) for each one of the aerial images, producing a count of the number of hybrid corn seed production plants in the male rows or producing a count of the number of hybrid corn seed production plants in the female rows;

storing the counts produced in c) on a tangible computer-accessible storage medium of the ground control station;

associating each one of the counts produced in c) with a corresponding geolocation;

producing a spot map, a zone map, or a heat map using the geolocations; and displaying the spot map, the zone map or the heat map on a display of the ground control station;

wherein prior to classifying each one of the identified rows of hybrid corn seed production plants, analyzing each one of the aerial images to identify one or more physical characteristics of the hybrid corn seed production plants in each row and/or analyzing each one of the aerial images to identify one or more physical characteristics of each row of the hybrid corn seed production plants; and classifying each one of the identified rows of hybrid corn seed production plants as either male or female based on the one or more identified physical characteristics of the hybrid corn seed production plants in each row and/or based on the one or more identified physical characteristics of each row of the hybrid corn seed production plants.

* * * * *